(12) United States Patent
Takiguchi et al.

(10) Patent No.: US 6,733,905 B2
(45) Date of Patent: May 11, 2004

(54) METAL COORDINATION COMPOUND, LUMINESCENCE DEVICE AND DISPLAY APPARATUS

(75) Inventors: Takao Takiguchi, Tokyo (JP); Shinjiro Okada, Isehara (JP); Akira Tsuboyama, Sagamihara (JP); Koji Noguchi, Sagamihara (JP); Takashi Moriyama, Kawasaki (JP); Jun Kamatani, Kawasaki (JP); Manabu Furugori, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/995,610

(22) Filed: Nov. 29, 2001

(65) Prior Publication Data

US 2002/0094453 A1 Jul. 18, 2002

(30) Foreign Application Priority Data

Nov. 29, 2000 (JP) ........................ 2000-362150
Nov. 9, 2001 (JP) ........................ 2001-344550

(51) Int. Cl.$^7$ ........................ H05B 33/14; C09K 11/06
(52) U.S. Cl. ........................ 428/690; 428/917; 313/504; 252/301.16; 546/4; 548/103
(58) Field of Search ................ 428/690, 917; 313/504; 252/301.16; 546/2, 4, 10, 152, 255; 548/101, 103, 108, 156, 217, 304.4, 312.7, 365.1

(56) References Cited

U.S. PATENT DOCUMENTS

| | | | |
|---|---|---|---|
| 5,698,858 A | 12/1997 | Börner | 250/484.2 |
| 5,756,224 A | 5/1998 | Börner et al. | 428/690 |
| 2002/0182441 A1 * | 12/2002 | Lamansky et al. | 428/690 |

FOREIGN PATENT DOCUMENTS

| | | |
|---|---|---|
| JP | 8-319482 | 12/1996 |
| JP | 11-256148 | 9/1999 |
| JP | 11-329739 | 11/1999 |

OTHER PUBLICATIONS

D.F. O'Brien et al., "Improved Energy Transfer in Electrophosphorescent Devices," 74(3) *Applied Phys. Lett.* 442–444 (Jan. 18, 1999).

M.A. Baldo et al. "Very High–Efficiency Green Organic Light–Emitting Devices Based on Electrophosphorescence," 75 (1) *Applied Phys. Lett.* 4–6 (Jul. 5, 1999).

C.H. Chen et al., "Recent Developments in Molecular Organic Electroluminescent Materials," 125 *Macromol. Symp.* 1–48 (1997), (no month).

* cited by examiner

Primary Examiner—Marie Yamnitzky
(74) Attorney, Agent, or Firm—Fitzpatrick, Cella, Harper & Scinto

(57) ABSTRACT

A metal coordination compound suitable as an organic material for a luminescent device is represented by the following formula (1):

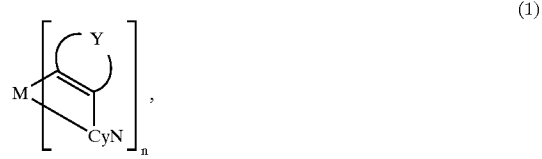

(1)

wherein M denotes Ir, Pt, Rh or Pd; n is 2 or 3; Y denotes an alkylene group having 2–6 carbon atoms capable of including one or at least two non-neighboring methylene groups which can be replaced with —O—, —S—, —C(O)—, —C(O)—O— or —O—C(O)— and capable of including a hydrogen atom which can be replaced with a linear or branched alkyl group which has 1–10 carbon atoms and is capable of including a hydrogen atom which can be replaced with fluorine atom; and CyN denotes a cyclic group containing a nitrogen atom connected to M and capable of having a substituent selected from the group consisting of a halogen atom; a nitro group; a phenyl group; a trialkylsilyl group having 1–8 carbon atoms; and a linear or branched alkyl group having 1–20 carbon atoms capable of including one or at least two non-neighboring methylene groups which can be replaced with —O—, —S—, —C(O)—, —C(O)—O—, —O—C(O)—, —CH=CH— or —C≡C— and capable of including a hydrogen atom which can be replaced with a fluorine atom.

8 Claims, 3 Drawing Sheets

METAL COORDINATION COMPOUND, LUMINESCENCE DEVICE AND DISPLAY APPARATUS

FIELD OF THE INVENTION AND RELATED ART

The present invention relates to a metal coordination compound, an electrical device using the metal coordination compound and a display apparatus using the device. More specifically, the present invention relates to an organic metal coordination compound having a formula (1) appearing hereinafter as a luminescence material so as to allow high luminance for a long period of time, an organic luminescence device using the metal coordination compound and a display apparatus including the luminescence device.

An organic electroluminescence (EL) device has been extensively studied as a luminescence device with a high responsiveness and high efficiency.

The organic EL device generally has a sectional structure as shown in FIGS. 1A or 1B (e.g., as described in "Macromol. Symp.", 125, pp. 1–48 (1997)).

Referring to the figures, the EL device generally has a structure including a transparent substrate 15, a transparent electrode 14 disposed on the transparent substrate 15, a metal electrode 11 disposed opposite to the transparent electrode 14, and a plurality of organic (compound) layers, as luminescence function layers, disposed between the transparent electrode 14 and the metal electrode 11.

Referring to FIG. 1A, the EL device in this embodiment has two organic layers including a luminescence layer 12 and a hole transport layer 13.

The transparent electrode 14 may be formed of a film of ITO (indium tin oxide) having a larger work function to ensure a good hole injection performance into the hole transport layer. On the other hand, the metal electrode 11 may be formed of a layer of aluminum, magnesium, alloys thereof, etc., having a smaller work function to ensure a good electron injection performance into the organic layer (s).

These (transparent and metal) electrodes 14 and 11 may be formed in a thickness of 50–200 nm.

The luminescence layer 12 may be formed of, e.g., aluminum quinolinol complex (representative example thereof may include Alq3 described hereinafter) having an electron transporting characteristic and a luminescent characteristic. The hole transport layer 13 may be formed of, e.g., biphenyldiamine derivative (representative example thereof may include α-NPD described hereinafter) having an electron donating characteristic.

The above-described EL device exhibits a rectification characteristic, so that when an electric field is applied between the metal electrode 11 as a cathode and the transparent electrode 14 as an anode, electrons are injected from the metal electrode 11 into the luminescence layer 12 and holes are injected from the transparent electrodes 14.

The thus-injected holes and electrons are recombined within the luminescence layer 12 to produce excitons placed in an excited state, thus causing luminescence at the time of transition of the excitons to a ground state. At that time, the hole transport layer 13 functions as an electron-blocking layer to increase a recombination efficiency at the boundary between the luminescence layer 12 and the hole transport layer 13, thus enhancing a luminescence efficiency.

Referring to FIG. 1B, in addition to the layers shown in FIG. 1A, an electron transport layer 16 is disposed between the metal electrode 11 and the luminescence layer 12, whereby an effective carrier blocking performance can be ensured by separating functions of luminescence, electron transport and hole transport, thus allowing effective luminescence.

The electron transport layer 16 may be formed of, e.g., oxadiazole derivatives.

In ordinary organic EL devices, fluorescence caused during a transition of luminescent center molecule from a singlet excited state to a ground state is used as luminescence.

On the other hand, different from the above fluorescence (luminescence) via singlet exciton, phosphorescence (luminescence) via triplet exciton has been studied for use in organic EL device as described in, e.g., "Improved energy transfer in electrophosphorescent device" (D. F. O'Brien et al., Applied Physics Letters, Vol. 74, No. 3, pp. 442–444 (1999)) and "Very high-efficiency green organic light-emitting devices based on electrophosphorescence" (M. A. Baldo et al., Applied Physics Letters, Vol. 75, No. 1, pp. 4–6 (1999)).

The EL devices shown in these documents may generally have a sectional structure shown in FIG. 1C.

Referring to FIG. 1C, four organic layers including a hole transfer layer 13, a luminescence layer 12, an exciton diffusion-prevention layer 17, and an electron transport layer 16 are successively formed in this order on the transparent electrode (anode) 14.

In the above documents, higher efficiencies have been achieved by using four organic layers including a hole transport layer 13 of α-NPD (shown below), an electron transport layer 16 of Alq3 (shown below), an exciton diffusion-prevention layer 17 of BPC (shown below), and a luminescence layer 12 of a mixture of CPB (shown below) as a host material with Ir(ppy)₃ (shown below) or PtOEP (shown below) as a guest phosphorescence material doped into CBP at a concentration of ca. 6 wt. %.

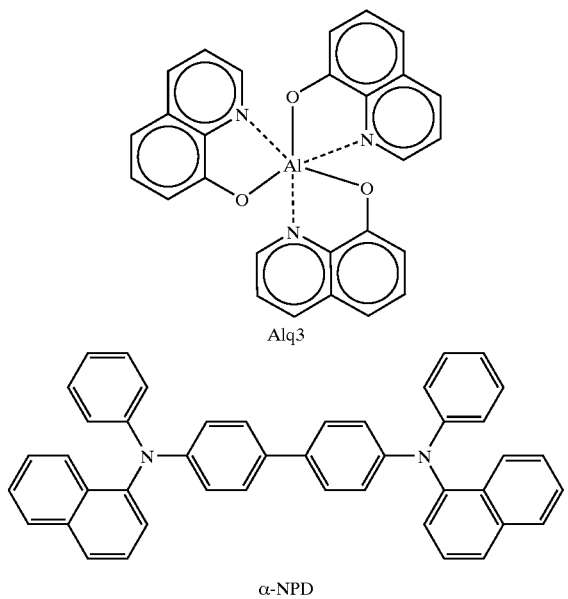

Alq3

α-NPD

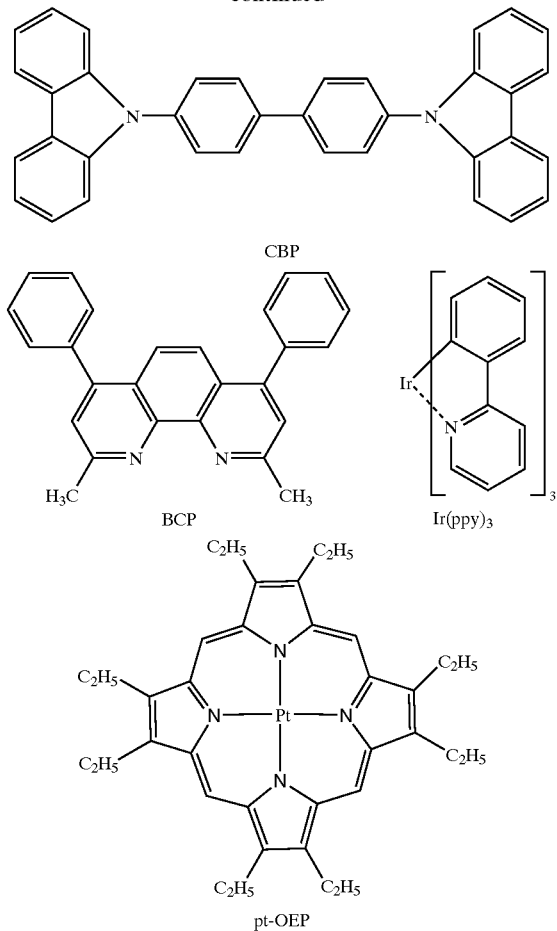

CBP

BCP

Ir(ppy)₃ pt-OEP

Alq3: tris(8-hydroxyquinoline) aluminum (aluminum-quinolinol complex),

α-NPD: N4,N4'-di-naphthalene-1-yl-N4,N4'-diphenyl-biphenyl-4,4'-diamine (4,4'-bis[N-(1-naphthyl)-N-phenyl-amino]biphenyl), CBP: 4,4'-N,N'-dicarbazole-biphenyl, BCP: 2,9-dimethyl-4,7-diphenyl-1,10-phenan-throline, Ir(ppy)₃: fac tris(2-phenylpyridine)iridium (iridium-phenylpyridine complex), and PtOEP: 2,3,7,8,12,13,17,18-octaethyl-21H,23H-porphine platinum (platinum-octaethyl porphine complex).

The phosphorescence (luminescence) material used in the luminescence layer 12 has particularly attracted notice. This is because the phosphorescence material is expected to provide a higher luminescence efficiency in principle.

More specifically, in the case of the phosphorescence material, excitons produced by recombination of carriers comprise singlet excitons and triplet excitons presented in a ratio of 1:3. For this reason, when fluorescence caused during the transition from the singlet excited state to the ground state is utilized, a resultant luminescence efficiency is 25% (as upper limit) based on all the produced excitons in principle.

On the other hand, in the case of utilizing phosphorescence caused during transition from the triplet excited state, a resultant luminescence efficiency is expected to be at least three times that of the case of fluorescence in principle. In addition thereto, if intersystem crossing from the singlet excited state (higher energy level) to the triplet excited state is taken into consideration, the luminescence efficiency of phosphorescence can be expected to be 100% (four times that of fluorescence) in principle.

The use of phosphorescence based on transition from the triplet excited state has also been proposed in, e.g., Japanese Laid-Open Patent Application (JP-A) 11-329739, JP-A 11-256148 and JP-A 8-319482.

However, the above-mentioned organic EL devices utilizing phosphorescence have accompanied with problems of a lower luminescence efficiency and stability thereof (luminescent deterioration) particularly in an energized state.

The reason for luminescent deterioration has not been clarified as yet but may be attributable to such a phenomenon that the life of triplet exciton is generally longer than that of singlet exciton by at least three digits, so that molecule is placed in a higher-energy state for a long period to cause reaction with ambient substance, formation of exciplex or excimer, change in minute molecular structure, structural change of ambient substance, etc.

Accordingly, the (electro)phosphorescence EL device is expected to provide a higher luminescence efficiency as described above, while the EL device is required to suppress or minimize the luminescent deterioration in energized state affecting the life of the EL device.

SUMMARY OF THE INVENTION

An object of the present invention is to provide a metal coordination compound as a material suitable for an organic layer for luminescence device (as an electrical device) capable of providing a high-efficiency luminescent state at a high brightness (or luminance) for a long period while minimizing the deterioration in luminescence in energized state.

Another object of the present invention is to provide an organic luminescence device including the metal coordination compound.

A further object of the present invention is to provide a display apparatus including the organic luminescence device.

According to the present invention, there is provided a metal coordination compound represented by the following formula (1):

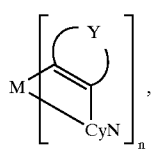

(1)

wherein M denotes Ir, Pt, Rh or Pd; n is 2 or 3; Y denotes an alkylene group having 2–6 carbon atoms capable of including one or at least two non-neighboring methylene groups which can be replaced with —O—, —S—, —C(O)—, —C(O)—O— or —O—C(O)— and capable of including a hydrogen atom which can be replaced with a linear or branched alkyl group which has 1–10 carbon atoms and is capable of including a hydrogen atom which can be replaced with fluorine atom; and CyN denotes a cyclic group containing a nitrogen atom connected to M and capable of having a substituent selected from the group consisting of a halogen atom; a nitro group; a phenyl group; a trialkylsilyl group having 1–8 carbon atoms; and a linear or branched alkyl group having 1–20 carbon atoms capable of including one or at least two non-neighboring methylene groups which can be replaced with —O—, —S—, —C(O)—, —C(O)—O—, —O—C(O)—, —CH═CH— or —C≡C— and capable of including a hydrogen atom which can be replaced with a fluorine atom.

The metal coordination compound of the present invention exhibits phosphorescence at the time of energy transfer from an excited state to a ground state to provide a high luminescence efficiency.

According to the present invention, there is also provided an electrical device, comprising: a substrate, a first electrode disposed on the substrate, an organic compound layer disposed on the first electrode, and a second electrode disposed on the organic compound layer, the organic compound layer comprising a metal coordination compound represented by the following formula (1):

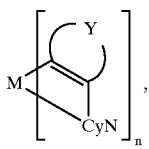

(1)

wherein M denotes Ir, Pt, Rh or Pd; n is 2 or 3; Y denotes an alkylene group having 2–6 carbon atoms capable of including one or at least two non-neighboring methylene groups which can be replaced with —O—, —S—, —C(O)—, —C(O)—O— or —O—C(O)— and capable of including a hydrogen atom which can be replaced with a linear or branched alkyl group which has 1–10 carbon atoms and is capable of including a hydrogen atom which can be replaced with a fluorine atom; and CyN denotes a cyclic group containing a nitrogen atom connected to M and capable of having a substituent selected from the group consisting of a halogen atom; a nitro group; a phenyl group; a trialkylsilyl group having 1–8 carbon atoms; and a linear or branched alkyl group having 1–20 carbon atoms capable of including one or at least two non-neighboring methylene groups which can be replaced with —O—, —S—, —C(O)—, —C(O)—O—, —O—C(O)—, —CH═CH— or —C≡C— and capable of including a hydrogen atom which can be replaced with a fluorine atom.

By applying a voltage between the pair of electrodes of the organic luminescence device to cause phosphorescence from the organic compound layer (luminescence function layer) containing the metal coordination compound.

According to the present invention, there is further provided an image display apparatus including the organic luminescence device and voltage application means for applying a voltage to the organic luminescence device.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Figure 1A:
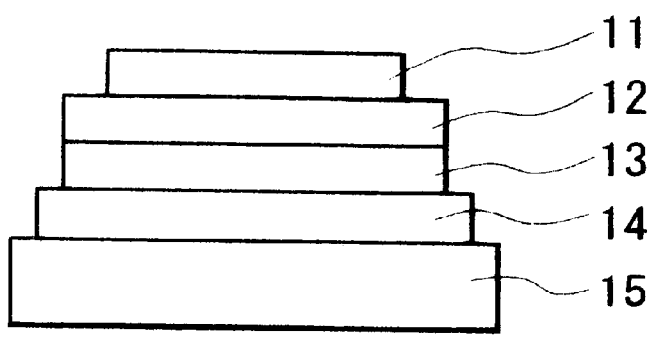
FIGS. 1A, 1B and 1C are respectively a schematic sectional view of a layer structure of an organic luminescence device.

In the case where a luminescence layer for an organic EL device is formed of a carrier transporting host material and a phosphorescent guest material, a process of emission of light (phosphorescence) may generally involve the following steps:

(1) transport of electron and hole within a luminescence layer,
(2) formation of exciton of the host material,
(3) transmission of excited energy between host material molecules,
(4) transmission of excited energy from the host material molecule to the guest material molecule,
(5) formation of triplet exciton of the guest material, and
(6) emission of light (phosphorescence) caused during transition from the triplet excited state to the ground state of the guest material.

In the above steps, desired energy transmission and luminescence may generally be caused based on various quenching and competition.

In order to improve a luminescence efficiency of the EL device, a luminescence center material per se is required to provide a higher yield of luminescence quantum. In addition thereto, an efficient energy transfer between host material molecules and/or between host material molecule and guest material molecule is also an important factor.

Further, the above-described luminescent deterioration in energized state may presumably relate to the luminescent center material per se or an environmental change thereof by its ambient molecular structure.

For this reason, our research group has extensively investigated an effect of use of the metal coordination compound of formula (1) as the luminescent center material and as a result, has found that the metal coordination compound of formula (1) allows a high-efficiency luminescence with a high brightness (luminance) for a long period (i.e., a decreased luminescent deterioration in energized state).

In the formula (1) for the metal coordination compound of the present invention, CyN may preferably be a cyclic group having a ring structure selected from the group consisting of pyridine, quinoline, imidazole, pyrazole, benzothiazole, benzoxazole, and benzimidazole, and capable of having said substituent. CyN may more preferably have a ring structure comprising pyridine or quinoline capable of having a substituent.

The metal coordination compound represented by the above formula (1) according to the present invention causes phosphorescence (luminescence) and is assumed to have a lowest excited state comprising a triplet excited state liable to cause metal-to-ligand charge transfer (MLCT* state) or π-π* state. The phosphorescent emission of light (phosphorescence) is caused to occur during the transition from the MLCT* state or π-π* state to the ground state.

The metal coordination compound of formula (1) according to the present invention has been found to provide a higher phosphorescence yield of 0.15–0.9 and a shorter phosphorescence life of 1–40 μsec.

The shorter phosphorescence life is necessary to provide a resultant EL device with a higher luminescence efficiency. This is because the longer phosphorescence life increases molecules placed in their triplet excited state which is a waiting state for phosphorescence, thus lowering the resultant luminescence efficiency particularly at a higher current density.

Accordingly, the metal coordination compound of formula (1) according to the present invention is a suitable luminescent material for an organic EL device with a higher phosphorescence yield and a shorter phosphorescence life.

Further, by appropriately selecting a combination of the alkene-diyl group forming a cyclic group (cycloalkene group) with alkylene group

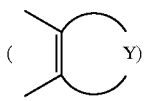

and the N-containing cyclic group (CyN) constituting the metal coordination compound of formula (1), it is possible to expect a controlled luminescence wavelength ranging from a shorter wavelength to a longer wavelength. Also from this viewpoint, the metal coordination compound of formula (1) of the present invention is suitable luminescent material for an organic EL device.

In the case of phosphorescent (luminescent) material, luminescent characteristics are largely affected by its molecular environment. On the other hand, principal characteristics of the fluorescent material are studied based on photoluminescence.

For this reason, results of photoluminescence of the phosphorescent material do not reflect luminescent characteristics of the resultant EL device in many cases since the luminescent characteristics in the case of the phosphorescent material depend on a magnitude of polarity of ambient host material molecules, ambient temperature, presence state of the material (e.g., solid state or liquid state), etc. Accordingly, different from the fluorescent material, it is generally difficult to expect the resultant EL characteristics for the phosphorescent material by simply removing a part of characteristics from results of photoluminescence characteristics.

Further, as substantiated in Examples appearing hereinafter, it has been clarified that the metal coordination compound of formula (1) of the present invention exhibits an excellent stability. This may be attributable to an intermolecular interaction based on incorporation of the cycloalkene group into the ligand of the metal coordination compound of formula (1). Specifically, an intermolecular interaction of molecules of the metal coordination compound of formula (1) with molecules of, e.g., the ambient host material is controlled by the incorporated cycloalkene group, thus allowing suppression of formation of excited association structure causing thermal quenching (deactivation). As a result, quenching step is reduced thereby to improve the resultant device characteristics.

Figure 1B:
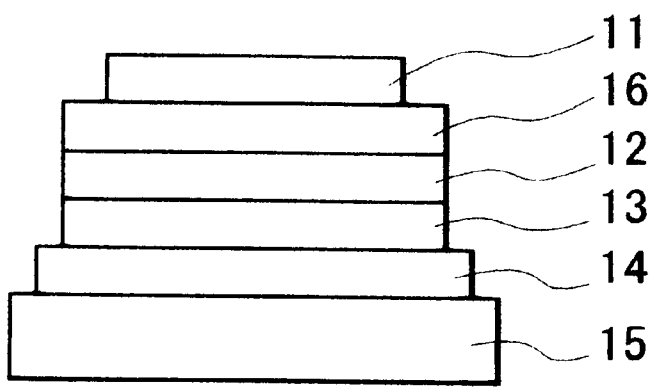
Figure 1C:
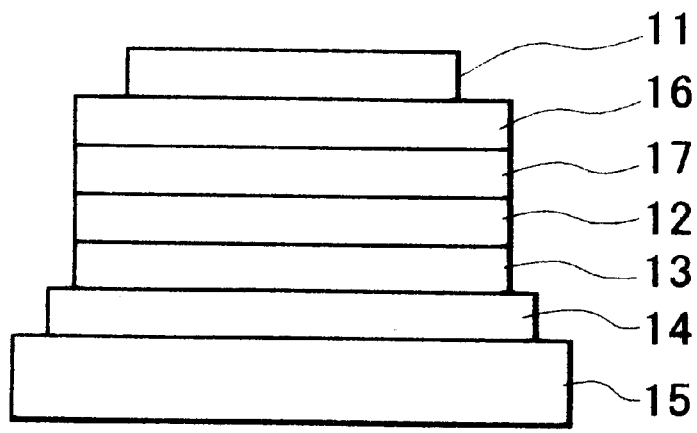

The organic luminescence device of the present invention may preferably be an electric field-luminescence device as shown in FIGS. 1A to 1C wherein a voltage is applied between a pair of electrodes sandwiching an organic (compound) layer containing the metal coordination compound of formula (1) to cause luminescence from the organic layer.

The metal coordination compound of formula (1) according to the present invention may, e.g., be synthesized through the following reaction schemes. In this case, Y is trimethylene and CyN is substituted pyridine.

<Synthesis of ligand L>

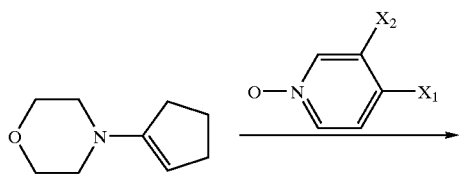

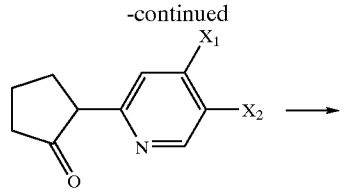

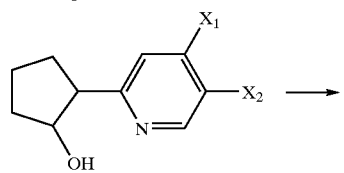

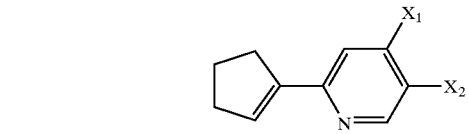

<Synthesis of Ir complex>

(a)

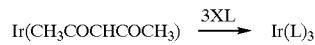

(b)

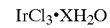

Synthesis Example

Synthesis of Example Compound No. (2) Appearing Hereinbelow

Step (i)

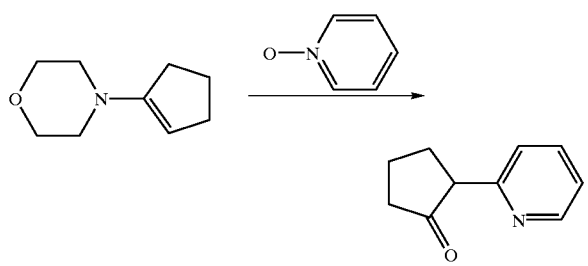

In a 2 liter-three-necked flask, 114 g (1.20 M) of pyridine-N-oxide and 720 ml of dry methylene chloride were placed in an argon gas stream atmosphere. To the mixture, 168 g (1.20 M) of benzoyl chloride was added dropwise in ca. 30 min. while stirring on an ice bath at 0° C. or below.

After further stirring for 30 min. at the same temperature, a solution of 221 g (1.44 M) of N-(1-cyclopentene-1-yl) morpholine in 360 ml of dry methylene chloride was added dropwise in ca. 1 hour to the mixture. The system was gradually warmed to room temperature, followed by refluxing for 5 hours under stirring.

After the reaction, the solvent was distilled off from the reaction mixture under reduced pressure to obtain a residue. To the residue, 1440 ml of 20%-hydrochloric acid was added, followed by washing with ether. To the aqueous layer, 1N-sodium hydroxide aqueous solution was added until the system showed pH=8, followed by extraction with methylene chloride. The organic layer was dried with anhydrous sodium sulfate and subjected to distilling-off of the solvent under reduced pressure to obtain a residue. The residue was subjected to vacuum distillation under reduced pressure to obtain 80.0 g of 2-(2-pyridyl)-cyclohentanone (boiling point: 65–67° C. (at 6.7 Pa)) (Yield: 41.4%).

Step (ii)

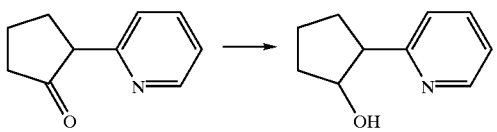

In an argon gas stream atmosphere, 80.0 g (496 mM) of 2-(2-pyridyl)cyclopentanone and 1600 ml of dry ethanol were placed in a 2 liter-three-necked flask, followed by stirring at room temperature and then addition thereto of 18.7 g (496 mM) of sodium boronhydride. The system was then stirred for 2 hours at room temperature, followed by addition thereto of a small amount of acetic acid and water. The reaction mixture was methylene chloride. The organic layer was dried with anhydrous sodium sulfate and subjected to distilling-off of the solvent under reduced pressure to obtain a residue. The residue was purified by silica gel column chromatography (eluent: hexane/ethyl acetate=3/1) to obtain 61.0 g of 1-hydroxy-2-(2-pyridyl)cyclopentane (Yield: 75.3%)

Step (iii)

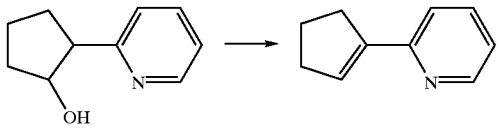

In an autoclave, 60.0 g (368 mM) of 1-hydroxy-2-(2-pyridyl)cyclopentane was placed and stirred for 60 hours at 170° C., followed by cooling, addition of water and extraction with methylene chloride. The organic layer was dried with anhydrous sodium sulfate, followed by distilling-off of the solvent under reduced pressure and then purification by silica gel column chromatography (eluent: hexane/ethyl acetate=8/1) to obtain 28.0 g of liquid 1-(2-pyridyl)cyclopentene (Yield: 52.5%).

Step (iv)

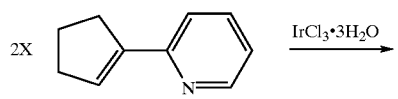

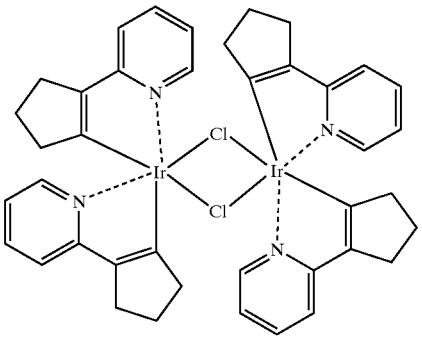
-continued

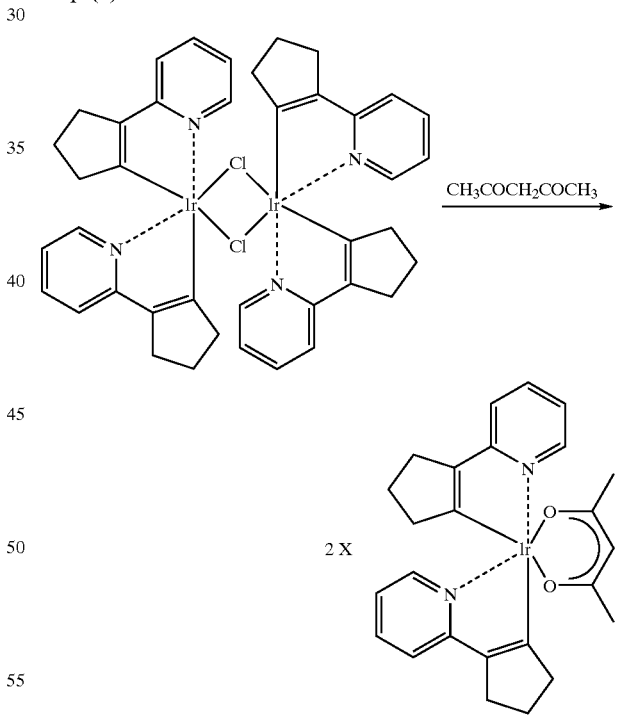

In a 200 ml-three-necked flask, 0.60 g (1.70 mM) of iridium (III) chloride, 1.10 g (7.58 mM) of 2-(2-pyridyl)cyclopentene, 50 ml of ethoxyethanol and 20 ml of water were placed and stirred for 0.5 hour at room temperature in a nitrogen gas stream atmosphere, followed by refluxing for 24 hours under stirring.

After the reaction, the reaction mixture was cooled to room temperature. The resultant precipitate was recovered by filtration and successively washed with water, ethanol and acetone, followed by drying under reduced pressure at room temperature to obtain 0.72 g of tetrakis[1-(2-pyridyl)cyclopentene-N,C$^2$](μ-dichloro)diiridium (III) (pale yellow powder) (Yield: 82.0%).

Step (v)

In a 200 ml-three-necked flask, 70 ml of ethoxyethanol, 0.70 g (0.68 mM) of tetrakis[1-(2-pyridyl)cyclopentene-N, C$^2$](μ-dichloro)diiridium (III), 0.21 g (2.10 mM) of acetylacetone and 1.02 g (9.62 mM) of sodium carbonate were placed and stirred at room temperature in a nitrogen gas stream atmosphere, followed by refluxing for 15 hours under stirring.

After the reaction, the reaction mixture was cooled on an ice bath. The resultant precipitate was recovered by filtration and washed with water. The resultant precipitate was purified by silica gel column chromatography (eluent: chloroform/methanol=30/1) to obtain 0.43 g of bis[1-(2-pyridyl)cyclopentene-N,$C^2$](acetylacetonato)iridium (III) (pale yellow powder) (Yield: 54.7%).

Step (vi)

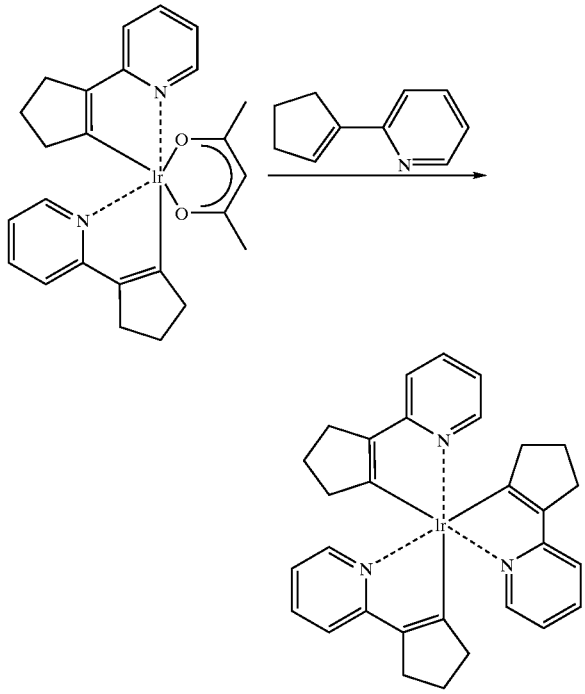

In a 200 ml-three-necked flask, 0.41 g (0.71 mM) of bis[1-(2-pyridyl)cyclopentene-N,$C^2$](acetylacetonato) iridium (III), 0.25 g (1.72 mM) of 1-(2-pyridyl)cyclopentene and 55 ml of glycerol were placed and stirred for 8 hours at ca. 180° C. in a nitrogen gas stream atmosphere.

After the reaction, the reaction mixture cooled to room temperature was poured into 350 ml of 1N-hydrochloric acid. The resultant precipitate was recovered by filtration, washed with water and dried for 5 hour at 100° C. under reduced pressure. The resultant dried residue was purified by silica gel column chromatography (eluent: chloroform) to obtain 0.43 g of bis[1-(2-pyridyl)cyclopentene-N,$C^2$] iridium (III) (Ex. Comp. No. (2); pale yellow powder) (Yield: 38.5%).

The thus-obtained metal coordination compound of formula (1) (Ex. Comp. No. (2)) was then subjected to MALDI-TOF-MS (matrix-assisted laser desorption ionization-time of flight mass spectrometry), whereby it was confirmed that the metal coordination compound has $M^+$ of 624.8.

In order to confirm that the luminescence was phosphorescence, the metal coordination compound of formula (1) (Ex. Comp. No. (2)) was dissolved in chloroform to prepare a first solution and a second solution. The first solution was subjected to aeration with oxygen gas and the second solution was subjected to aeration with nitrogen gas.

When the thus-prepared first and second solutions were subjected to light irradiation, the oxygen-aerated solution exhibited substantially no photoluminescence but the nitrogen-aerated solution exhibited photoluminescence. As a result, the metal coordination compound of formula (1) of the present invention was found to be a phosphorescent metal coordination compound.

The metal coordination compound of formula (1) (Ex. Comp. No. (2)) was then subjected to measurement of luminescence life (time) in the following manner.

The metal coordination compound was dissolved in chloroform and was spin-coated on a quartz substrate to form a ca. 0.1 µm-thick metal coordination compound layer.

By using a luminescence life-measuring apparatus (available from Hamamatsu Photonics K.K.), the above-prepared metal coordination compound layer formed on the substrate was subjected to pulse irradiation with nitrogen laser light (excitation wavelength: 337 nm) at room temperature to measure an attenuation time immediately after the excitation laser pulse irradiation.

A luminescence intensity I after a lapse of t (sec) is defined as the following equation:

$$I = I_0 exp(-t/\tau),$$

wherein $I_0$ represents an initial luminescence intensity and $\tau$ (µsec) represents a luminescence life (time).

As a result, the metal coordination compound of formula (1) (Ex. Comp. No. (2)) showed a shorter luminescence life of at most 10 µsec. among ordinary luminescent materials.

Other metal coordination compounds of formula (1) of the present invention may be principally synthesized in a similar manner as in Synthesis Example described above.

Specific examples of the metal coordination compound of formula (1) of the present invention may include those shown in Table 1 below. The metal coordination compound of the present invention is, however, not restricted to these examples.

In Table 1, symbols B to G' and Pr to Bi: represent the following divalent groups, respectively.

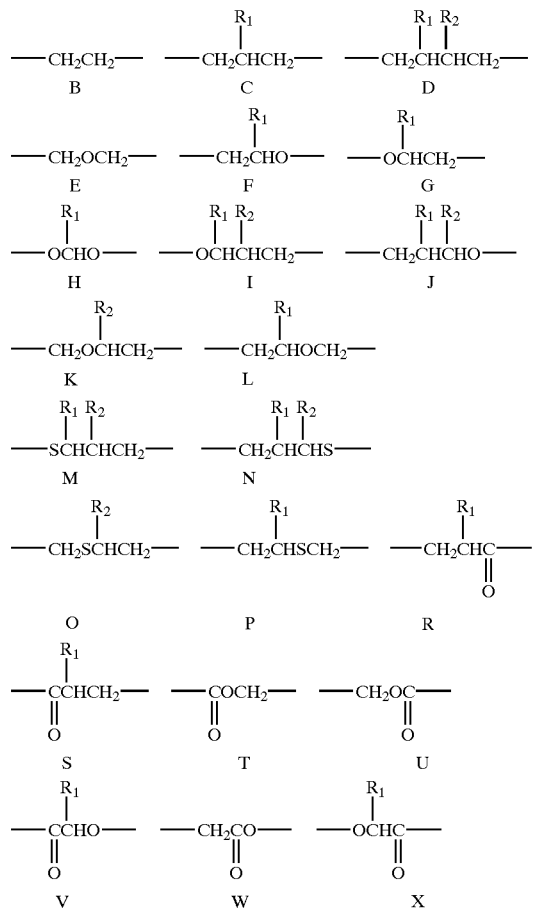

-continued

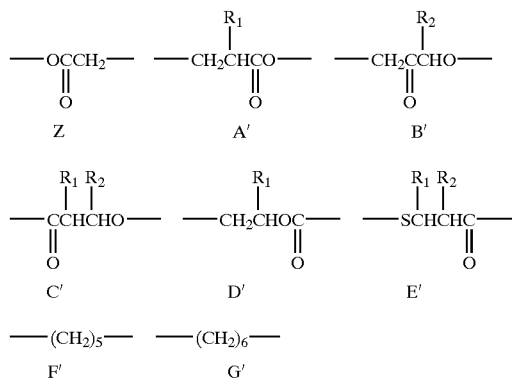

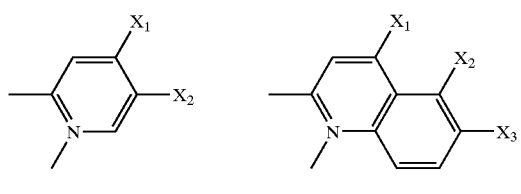

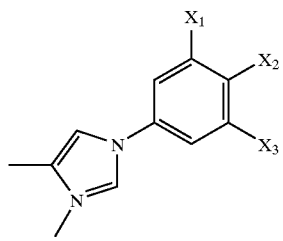

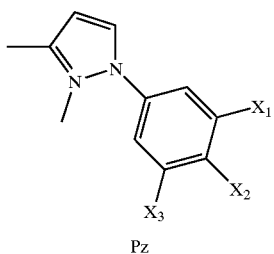

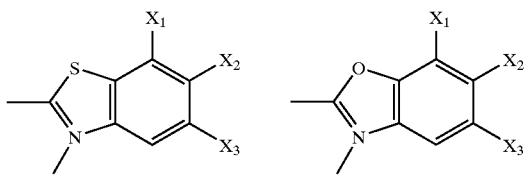

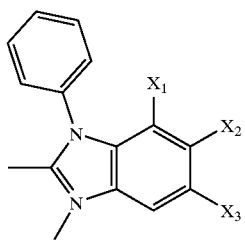

| No. | M | n | Y | $R_1$ | $R_2$ | CyN | $X_1$ | $X_2$ | $X_3$ |
|---|---|---|---|---|---|---|---|---|---|
| (1) | Ir | 3 | B | — | — | Pr | H | H | — |
| (2) | Ir | 3 | C | H | — | Pr | H | H | — |
| (3) | Ir | 3 | C | H | — | Pr | $OCH_3$ | H | — |
| (4) | Ir | 3 | C | H | — | Pr | H | $CF_3$ | — |
| (5) | Ir | 3 | C | H | — | Pr | H | $OCH_2C\equiv CCH_3$ | — |
| (6) | Ir | 3 | C | H | — | Pr | $C_3F_7$ | H | — |
| (7) | Ir | 3 | C | H | — | Pr | H | Cl | — |
| (8) | Ir | 3 | C | H | — | Pr | $CF_3$ | H | — |
| (9) | Ir | 3 | C | H | — | Pr | $CF_3$ | $CF_3$ | — |
| (10) | Ir | 3 | C | $CH_3$ | — | Pr | H | H | — |
| (11) | Ir | 3 | C | $C_2H_5$ | — | Pr | H | H | — |
| (12) | Ir | 3 | C | $C_2H_5$ | — | Pr | $OC_4H_9$ | H | — |
| (13) | Ir | 3 | C | $C_3H_7$ | — | Pr | H | H | — |
| (14) | Ir | 3 | C | $C_3H_7$ | — | Pr | H | $OCH(CH_3)_2$ | — |
| (15) | Ir | 3 | C | $C_4H_9$ | — | Pr | H | H | — |
| (16) | Ir | 3 | C | $C_4H_9$ | — | Pr | H | Br | — |
| (17) | Ir | 3 | C | $C_4H_9$ | — | Pr | H | $NO_2$ | — |
| (18) | Ir | 3 | C | $C_6H_{13}$ | — | Pr | H | H | — |
| (19) | Ir | 3 | C | $C_6H_{13}$ | — | Pr | H | $Si(CH_3)_2C_4H_9$ | — |
| (20) | Ir | 3 | C | $C_7H_{15}$ | — | Pr | H | H | — |
| (21) | Ir | 3 | C | $C_8H_{17}$ | — | Pr | H | H | — |
| (22) | Ir | 3 | C | $C_9H_{19}$ | — | Pr | H | $COCH_3$ | — |
| (23) | Ir | 3 | C | $C_2F_5(CH_2)_6$ | — | Pr | H | H | — |
| (24) | Ir | 3 | C | $C_2H_5(CH_3)CH(CH_2)_4$ | — | Pr | H | H | — |
| (25) | Ir | 3 | D | H | H | Pr | H | H | — |
| (26) | Ir | 3 | D | H | H | Pr | $OC_8H_{17}$ | H | — |
| (27) | Ir | 3 | D | H | H | Pr | H | Cl | — |

-continued

| No. | M | n | Y | R₁ | R₂ | CyN | X₁ | X₂ | X₃ |
|---|---|---|---|---|---|---|---|---|---|
| (28) | Ir | 3 | D | H | H | Pr | CF₃ | H | — |
| (29) | Ir | 3 | D | H | H | Pr | CF₃ | CF₃ | — |
| (30) | Ir | 3 | D | H | H | Pr | H | OCH(CH₃)₂ | — |
| (31) | Ir | 3 | D | H | H | Pr | H | Br | — |
| (32) | Ir | 3 | D | H | H | Pr | H | NO₂ | — |
| (33) | Ir | 3 | D | CH₃ | H | Pr | H | H | — |
| (34) | Ir | 3 | D | CH₃ | CH₃ | Pr | H | H | — |
| (35) | Ir | 3 | D | H | CH₃ | Pr | H | H | — |
| (36) | Ir | 3 | D | H | CH₃ | Pr | H | CF₃ | — |
| (37) | Ir | 3 | D | C₃H₇ | H | Pr | H | H | — |
| (38) | Ir | 3 | D | C₄H₉ | H | Pr | H | H | — |
| (39) | Ir | 3 | D | C₆H₁₃ | H | Pr | H | H | — |
| (40) | Ir | 3 | D | C₇H₁₅ | H | Pr | CF₃ | H | — |
| (41) | Ir | 3 | D | C₈H₁₇ | H | Pr | H | OCH₂C≡CCH₃ | — |
| (42) | Ir | 3 | D | C₉H₁₉ | H | Pr | OCH₂CH=CH₂ | H | — |
| (43) | Ir | 3 | D | C₂F₅(CH₂)₆ | H | Pr | H | H | — |
| (44) | Ir | 3 | D | C₂H₅(CH₃)CH(CH₂)₄ | H | Pr | H | H | — |
| (45) | Ir | 3 | E | — | — | Pr | H | H | — |
| (46) | Ir | 3 | F' | — | — | Pr | H | H | — |
| (47) | Ir | 3 | G' | — | — | Pr | H | H | — |
| (48) | Ir | 3 | F | CH₃ | — | Pr | CF₃ | H | — |
| (49) | Ir | 3 | G | H | — | Pr | H | (CH₂)₄OCOC₃H₇ | — |
| (50) | Ir | 3 | H | C₄H₉ | — | Pr | H | Cl | — |
| (51) | Ir | 3 | C | C₆H₁₃ | — | Q | H | H | H |
| (52) | Ir | 3 | D | H | H | Q | H | H | H |
| (53) | Ir | 3 | F' | — | — | Q | H | H | C₃H₇ |
| (54) | Ir | 3 | G' | — | — | Q | H | H | H |
| (55) | Ir | 3 | I | H | CH₃ | Q | H | H | H |
| (56) | Ir | 3 | J | H | H | Q | H | H | OC₇H₁₅ |
| (57) | Ir | 3 | C | H | — | Iz | H | H | H |
| (58) | Ir | 3 | D | H | H | Iz | H | H | H |
| (59) | Ir | 3 | C | C₆H₁₃ | — | Pz | H | OCH₃ | H |
| (60) | Ir | 3 | D | H | CH₃ | Pz | OCH₃ | OCH₃ | OCH₃ |
| (61) | Ir | 3 | B | — | — | Bz | H | H | CF₃ |
| (62) | Ir | 3 | C | H | — | Bz | H | H | H |
| (63) | Ir | 3 | C | H | — | Bz | H | C₁₀H₂₁ | H |
| (64) | Ir | 3 | C | C₂H₅ | — | Bz | H | O(CH₂)₄C₃F₇ | H |
| (65) | Ir | 3 | D | H | H | Bz | H | H | H |
| (66) | Ir | 3 | D | H | H | Bz | H | F | F |
| (67) | Ir | 3 | D | H | H | Bz | H | OCH₃ | H |
| (68) | Ir | 3 | L | C₄H₉ | — | Bz | H | H | H |
| (69) | Ir | 3 | B | — | — | Bo | H | H | H |
| (70) | Ir | 3 | C | H | — | Bo | H | H | H |
| (71) | Ir | 3 | C | H | — | Bo | H | H | C₈H₁₇ |
| (72) | Ir | 3 | D | H | H | Bo | H | H | H |
| (73) | Ir | 3 | D | H | H | Bo | H | OCH₃ | H |
| (74) | Ir | 3 | K | — | C₂H₅ | Bo | H | H | CF₃ |
| (75) | Ir | 3 | L | CH₃ | — | Bo | H | H | C₁₁H₂₃ |
| (76) | Ir | 3 | M | H | CH₃ | Bo | H | H | H |
| (77) | Ir | 3 | C | H | — | Bi | H | H | H |
| (78) | Ir | 3 | C | H | — | Bi | H | OC₇H₁₅ | H |
| (79) | Ir | 3 | D | H | C₆H₁₃ | Bi | H | H | H |
| (80) | Ir | 3 | N | CH₃ | H | Bi | H | H | H |
| (81) | Pt | 2 | B | — | — | Pr | H | H | — |
| (82) | Pt | 2 | C | H | — | Pr | H | H | — |
| (83) | Pt | 2 | C | H | — | Pr | H | CF₃ | — |
| (84) | Pt | 2 | C | C₂H₅ | — | Pr | H | H | — |
| (85) | Pt | 2 | D | H | H | Pr | H | H | — |
| (86) | Pt | 2 | D | H | H | Pr | H | Cl | — |
| (87) | Pt | 2 | D | H | H | Pr | H | NO₂ | — |
| (88) | Pt | 2 | F' | — | — | Pr | CF₃ | CF₃ | — |
| (89) | Pt | 2 | G' | — | — | Pr | H | H | — |
| (90) | Pt | 2 | O | — | CH₃ | Pr | H | H | — |
| (91) | Pt | 2 | P | CH₃ | — | Pr | H | H | — |
| (92) | Pt | 2 | R | C₄H₉ | — | Pr | OCH₃ | H | — |
| (93) | Pt | 2 | S | H | — | Pr | H | H | — |
| (94) | Pt | 2 | T | — | — | Pr | H | H | — |
| (95) | Pt | 2 | U | — | — | Pr | H | H | — |
| (96) | Pt | 2 | C | C₈H₁₇ | — | Q | H | H | OCH₃ |
| (97) | Pt | 2 | V | C₃H₇ | — | Q | H | H | H |
| (98) | Pt | 2 | Z | — | — | Iz | H | COOC₃H₇ | H |
| (99) | Pt | 2 | A' | C₃H₇ | — | Pz | H | O(CH₂)₄C₃F₇ | H |
| (100) | Pt | 2 | C | H | — | Bz | H | H | O(CH₂)₃C≡CCH₃ |
| (101) | Pt | 2 | F' | — | — | Bz | H | F | H |
| (102) | Pt | 2 | D | CH₃ | H | Bo | H | H | C₆H₁₃ |
| (103) | Pt | 2 | B' | — | C₂H₅ | Bo | H | H | H |
| (104) | Pt | 2 | B | — | — | Bi | H | H | H |

-continued

| No. | M | n | Y | $R_1$ | $R_2$ | CyN | $X_1$ | $X_2$ | $X_3$ |
|---|---|---|---|---|---|---|---|---|---|
| (105) | Rh | 3 | B | — | — | Pr | H | H | — |
| (106) | Rh | 3 | C | H | — | Pr | H | H | — |
| (107) | Rh | 3 | C | H | — | Pr | $OC_8H_{17}$ | H | — |
| (108) | Rh | 3 | C | H | — | Pr | H | Cl | — |
| (109) | Rh | 3 | C | H | — | Pr | $CF_3$ | H | — |
| (110) | Rh | 3 | C | H | — | Pr | $CF_3$ | $CF_3$ | — |
| (111) | Rh | 3 | C | $C_4H_9$ | — | Pr | H | H | — |
| (112) | Rh | 3 | C | $C_6H_{13}$ | — | Pr | H | H | — |
| (113) | Rh | 3 | C | $C_6H_{13}$ | — | Pr | H | $NO_2$ | — |
| (114) | Rh | 3 | C | $C_7H_{15}$ | — | Pr | H | H | — |
| (115) | Rh | 3 | C | $C_2F_5(CH_2)_6$ | — | Pr | H | H | — |
| (116) | Rh | 3 | D | H | H | Pr | H | H | — |
| (117) | Rh | 3 | D | H | H | Pr | H | $Si(CH_3)_2C_4H_9$ | — |
| (118) | Rh | 3 | D | H | H | Pr | $SC_3H_7$ | H | — |
| (119) | Rh | 3 | D | H | H | Pr | H | $OCH(CH_3)_2$ | — |
| (120) | Rh | 3 | D | $CH_3$ | H | Pr | H | $COC_4H_9$ | — |
| (121) | Rh | 3 | D | $CH_3$ | $CH_3$ | Pr | H | H | — |
| (122) | Rh | 3 | D | H | $CH_3$ | Pr | H | H | — |
| (123) | Rh | 3 | D | H | $C_7H_{15}$ | Pr | H | $CF_3$ | — |
| (124) | Rh | 3 | G' | — | — | Pr | $OC_8H_{17}$ | H | — |
| (125) | Rh | 3 | C' | H | $C_8H_{17}$ | Pr | H | H | — |
| (126) | Rh | 3 | D' | $CH_3$ | — | Pr | H | H | — |
| (127) | Rh | 3 | E' | H | $CH_3$ | Pr | H | Br | — |
| (128) | Rh | 3 | H | H | — | Pr | H | H | — |
| (129) | Rh | 3 | F' | — | — | Pr | H | $Si(CH_3)_3$ | — |
| (130) | Rh | 3 | I | H | $CH_3$ | Pr | H | H | — |
| (131) | Rh | 3 | J | H | H | Pr | H | H | — |
| (132) | Rh | 3 | K | — | $C_4H_9$ | Pr | H | H | — |
| (133) | Rh | 3 | L | $C_2H_5$ | — | Pr | H | H | — |
| (134) | Rh | 3 | M | H | $CH_3$ | Pr | H | $CF_3$ | — |
| (135) | Rh | 3 | C | H | — | Q | H | H | $C_9H_{19}$ |
| (136) | Rh | 3 | D | H | H | Q | H | H | H |
| (137) | Rh | 3 | D | H | H | Q | H | H | Cl |
| (138) | Rh | 3 | F' | — | — | Q | H | H | H |
| (139) | Rh | 3 | C | H | — | Iz | $OCH_3$ | H | $OCH_3$ |
| (140) | Rh | 3 | N | H | $CH_3$ | Iz | H | $OC_{13}H_{27}$ | H |
| (141) | Rh | 3 | C | $C_4H_9$ | — | Pz | F | F | H |
| (142) | Rh | 3 | D | H | H | Pz | H | H | H |
| (143) | Rh | 3 | C | H | — | Bz | H | H | H |
| (144) | Rh | 3 | C | H | — | Bz | H | $O(CH_2)_2OCH_2C_2F_5$ | H |
| (145) | Rh | 3 | C | $C_6H_{13}$ | — | Bz | H | H | H |
| (146) | Rh | 3 | D | H | $CH_3$ | Bz | H | H | H |
| (147) | Rh | 3 | F' | — | — | Bz | H | $CF_3$ | H |
| (148) | Rh | 3 | C | H | — | Bo | H | H | H |
| (149) | Rh | 3 | C | $C_3H_7$ | — | Bo | H | H | H |
| (150) | Rh | 3 | D | H | H | Bo | H | H | H |
| (151) | Rh | 3 | D | H | H | Bo | H | H | $O(CH_2)_3C{\equiv}CCH_3$ |
| (152) | Rh | 3 | O | — | $CH_3$ | Bi | H | H | H |
| (153) | Pd | 2 | B | — | — | Pr | H | H | — |
| (154) | Pd | 2 | C | H | — | Pr | H | H | — |
| (155) | Pd | 2 | C | H | — | Pr | H | $CF_3$ | — |
| (156) | Pd | 2 | D | $C_7H_{15}$ | H | Pr | H | H | — |
| (157) | Pd | 2 | C | $C_2H_5$ | — | Q | H | H | $C_3H_7$ |
| (158) | Pd | 2 | D | $C_2F_5(CH_2)_6$ | H | Pz | H | H | H |
| (159) | Pd | 2 | C | $CH_3$ | — | Bz | H | $C_{10}H_{21}$ | H |
| (160) | Pd | 2 | D | H | $CH_3$ | Bo | H | H | $CF_3$ |
| (161) | Pd | 2 | C | H | — | Bi | H | $OC_5H_{11}$ | H |

Hereinbelow, the present invention will be described more specifically based on Examples.

EXAMPLES 1–12

Comparative Example 1

Thirteen organic luminescence devices (EL devices) were prepared in the following manner.

Each of the organic luminescence devices had a structure including three organic (compound) layers (luminescence function layers) shown in FIG. 1B.

On a 1.1 mm-thick alkali-free glass substrate (transparent substrate 15), a 100 nm-thick film (transparent electrode 14) of ITO (indium tin oxide) was formed by sputtering, followed by patterning to have an (opposing) electrode area of 3 mm².

On the ITO-formed substrate, three organic layers and two metal electrode layers shown below were successively formed by vacuum (vapor) deposition using resistance heating in a vacuum chamber ($10^{-4}$ Pa).

Organic layer 1 (hole transport layer 13) (40 nm): α-NPD

Organic layer 2 (luminescence layer 12) (30 nm): CBP/metal coordination compound of formula (1) shown in Table 2 (95/5 by weight) (co-vacuum deposition)

Organic layer 3 (electron transport layer 16) (30 nm): Alq3

Metal electrode layer 1 (metal electrode 11) (15 nm): Al—Li alloy (Li=1.8 wt. %)

Metal electrode layer 2 (metal electrode 11) (100 nm): Al

EL characteristics of the luminescence devices using the metal coordination compounds of formula (1) were measured by using a microammeter ("Model 4140B", mfd. by Hewlett-Packard Co.) for a current density under application of a voltage of 12 volts (current-voltage characteristic) and using a luminance meter ("Model BM7", mfd. by Topcon K.K.) for a luminescence luminance at room temperature. Further, both the above-prepared luminescence devices showed a good rectification characteristic.

For measurement, each of the above-prepared luminescence devices was taken out of the vacuum chamber and was subjected to a continuous energization test in an atmosphere of dry nitrogen gas stream so as to remove device deterioration factors, such as oxygen and moisture (water content).

Figure 3:
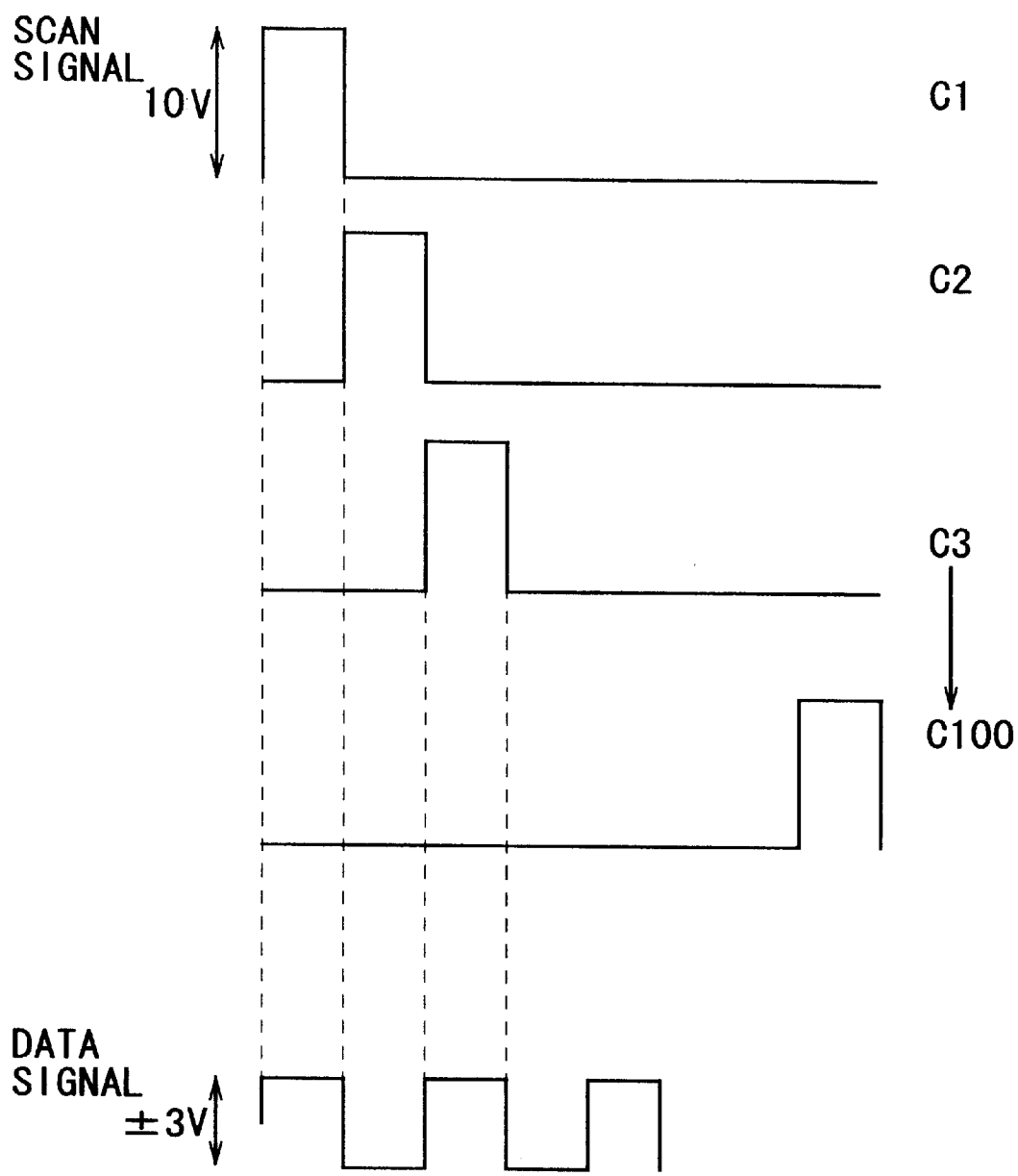
FIG. 3 is a waveform diagram of a driving signal employed in Example 13.

The continuous energization test was performed by continuously applying a drive voltage waveform shown in FIG. 3 at a constant current density of 70 mA/cm$^2$ to the luminescence device having the ITO (transparent) electrode (as an anode) and the Al (metal) electrode (as a cathode), followed by measurement of luminance (brightness) with time so as to determine a time (luminance half-life) required for decreasing an initial luminance (60–220 cd/m$^2$) to ½ thereof.

The results are shown in Table 2 below.

TABLE 2

| Ex. No. | Ex. Comp. No. | Luminance half-life (Hr) |
|---|---|---|
| 1 | (2) | 900 |
| 2 | (4) | 800 |
| 3 | (25) | 850 |
| 4 | (43) | 650 |
| 5 | (62) | 600 |
| 6 | (71) | 600 |
| 7 | (79) | 650 |
| 8 | (92) | 550 |
| 9 | (108) | 600 |
| 10 | (113) | 700 |
| 11 | (122) | 800 |
| 12 | (155) | 550 |
| Comp. Ex. 1 | Ir(ppy)3 | 350 |

As is apparent from Table 2, compared with the conventional luminescence device using Ir(ppy)$_3$ (Comp. Ex. 1), the luminescence devices using the metal coordination compounds of formula (1) according to the present invention provide longer luminance half-lifes, thus resulting in an EL device having a high durability (luminance stability) based on a good stability of the metal coordination compound of formula (1) of the present invention.

EXAMPLE 13

Figure 2:
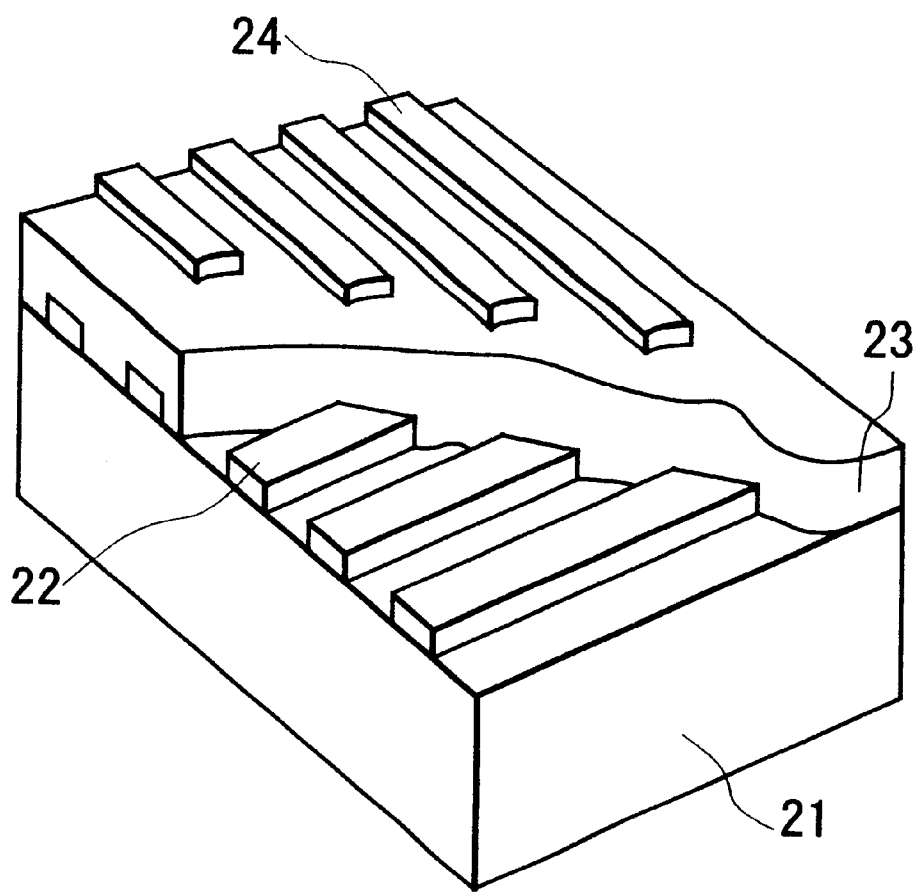
FIG. 2 is a schematic perspective view of an organic luminescence device (EL device) of a single matrix-type used in Example 13 appearing hereinafter.

A simple matrix-type organic EL device shown in FIG. 2 was prepared in the following manner.

On a 1.1 mm-thick glass substrate 21 (75×75 mm), a ca. 100 nm-thick transparent electrode 22 of ITO (as an anode) was formed by sputtering, followed by patterning in a stripe form comprising 100 lines (each having a width of 100 μm and a spacing of 40 μm).

On the ITO electrode 22, an organic lamination layer 23 including three organic layers was formed in the same manner as in Example 1 (using the metal coordination compound of formula (1) (Ex. Comp. No. (2)).

Then, on the organic lamination layer 23, a metal electrode comprising a 10 nm-thick Al—Li alloy layer (Li: 1.3 wt. %) and a 150 nm-thick Al layer (disposed on the Al—Li alloy layer) was formed by vacuum deposition (2.7×10$^{-3}$ Pa (=2×10$^{-5}$ Torr)) with a mask, followed by patterning in a stripe form comprising 100 lines (each having a width of 100 μm and a spacing of 40 μm) arranged to intersect the ITO stripe electrode lines at right angles, thus forming an organic EL device having a matrix of pixels (100×φpixels).

The thus-prepared organic EL device was placed in a glove box aerated with nitrogen gas and driven in a simple matrix manner (frame frequency: 30 Hz, interlace scanning) by applying a driving waveform (drive voltage: 7 to 13 volts, scanning signal voltage: 10 volts, data signal voltage: ±3 volts) as shown in FIG. 3.

As a result, a smooth motion picture display by the organic EL device was confirmed.

The organic luminescence device of the present invention may be applicable to flat panel displays based on its high-efficiency luminescence characteristics. As a result, it becomes possible to provide a flat panel display device having advantages, such as a good energy saving performance, high visibility and light weight properties.

When the organic luminescence device of the present invention is used as a light source for a printer, for example, the organic luminescence device is formed in a line form and disposed in proximity to a photosensitive drum, thus allowing independent drive of respective device elements as a line shutter to effect desired exposure to the photosensitive drum. Further, when the organic luminescence device of the present invention is used as an illumination device or a backlight for a liquid crystal display apparatus, compared with the case of an ordinary fluorescent lamp, the organic luminescence device is expected to exhibit an excellent energy saving effect.

In place of the organic luminescence device of the present invention of the simple matrix (XY matrix)-type, the organic luminescence device of the present invention may particularly suitably be employed in an image forming display apparatus of an active matrix-type including TFTs (thin film transistors).

As described hereinabove, according to the present invention, it is possible to provide a metal coordination compound of formula (1) exhibiting a higher phosphorescence yield and a shorter phosphorescence life (time) and allowing control of a maximum luminescence wavelength based on a combination of a cycloalkene group and an N-containing cyclic group (CyN). When the metal coordination compound of formula (1) is used as an organic (compound) layer of an organic luminescence device, the resultant organic luminescence device exhibits not only a high-efficiency luminescence but also a high luminance for a long period of time while suppressing a deterioration in luminescence in energized state.

Further, it becomes possible to provide an image forming apparatus using the organic luminescence device as a display device.

What is claimed is:

1. A metal coordination compound represented by the following formula (1):

(1)

wherein M denotes Ir, Pt, Rh or Pd; n is 2 or 3;

Y denotes an alkylene group having 2–6 carbon atoms in which one methylene group or at least two non-neighboring methylene groups can optionally be replaced with —O—, —S—, —C(O)—, —C(O)—O— or —O—C(O)—; and which said alkylene group includes a hydrogen atom optionally replaced with a linear or branched alkyl group having 1–10 carbon atoms; and which said alkylene group includes a hydrogen atom optionally replaced with a fluorine atom; and CyN denotes a cyclic group containing a nitrogen atom connected to M and optionally having a substituent selected from the group consisting of a halogen atom; a nitro group; a phenyl group; a trialkylsilyl group having 1–8 carbon atoms; and a linear or branched alkyl group having 1–20 carbon atoms in which one methylene group or at least two non-neighboring methylene groups can optionally be replaced with —O—, —S—, —C(O)—, —C(O)—O—, —O—C(O)—, —CH=CH— or C≡C—, and which said alkyl group includes a hydrogen atom optionally replaced with a fluorine atom.

2. A compound according to claim 1, wherein CyN in the formula (1) is a cyclic group having a ring structure selected from the group consisting of pyridine, quinoline, imidazole, pyrazole, benzothiazole, benzoxazole, and benzimidazole, and optionally having said substituent.

3. A compound according to claim 1 or 2, wherein M in the formula (1) is Ir.

4. An electrical device, comprising: a substrate, a first electrode disposed on the substrate, an organic compound layer disposed on the first electrode, and a second electrode disposed on the organic compound layer, the organic compound layer comprising a metal coordination compound represented by the following formula (1):

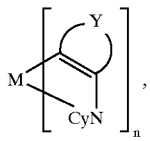

(1)

wherein M denotes Ir, Pt, Rh or Pd; n is 2 or 3;

Y denotes an alkylene group having 2–6 carbon atoms in which one methylene group or at least two non-neighboring methylene groups can optionally be replaced with —O—, —S—, —C(O)—, —C(O)—O— or —O—C(O)—; and which said alkylene group includes a hydrogen atom optionally replaced with a linear or branched alkyl group having 1–10 carbon atoms; and which said alkylene group includes a hydrogen atom optionally replaced with a fluorine atom; and CyN denotes a cyclic group containing a nitrogen atom connected to M and optionally having a substituent selected from the group consisting of a halogen atom; a nitro group; a phenyl group; a trialkylsilyl group having 1–8 carbon atoms; and a linear or branched alkyl group having 1–20 carbon atoms in which one methylene group or at least two non-neighboring methylene groups can optionally be replaced with —O—, —S—, —C(O)—, —C(O)—O—, —O—C(O)—, —CH=CH— or —C≡C—, and which said alkyl group includes a hydrogen atom optionally replaced with a fluorine atom.

5. A device according to claim 4, wherein CyN in the formula (1) is a cyclic group having a ring structure selected from the group consisting of pyridine, quinoline, imidazole, pyrazole, benzothiazole, benzoxazole, and benzimidazole, and optionally having said substituent.

6. A device according to claim 4, wherein M in the formula (1) is Ir.

7. A device according to any one of claims 4–6, wherein the organic compound layer luminesces when a voltage is applied between the first and second electrodes.

8. A display apparatus, comprising: an electrical device according to claim 7 and voltage application means for applying a voltage to the electrical device.

* * * * *

UNITED STATES PATENT AND TRADEMARK OFFICE
CERTIFICATE OF CORRECTION

PATENT NO. : 6,733,905 B2
DATED : May 11, 2004
INVENTOR(S) : Takao Takiguchi et al.

Page 1 of 1

It is certified that error appears in the above-identified patent and that said Letters Patent is hereby corrected as shown below:

Column 3,
Line 45, "phenan-throline," should read -- phenanthroline, --.

Column 4,
Line 9, "have" should read -- have been --.

Column 11,
Line 42, "hour" should read -- hours --.

Column 12,
Line 29, "Bi:" should read -- Bi --.

Column 20,
Line 3, "(100×φpixels)." should read -- 100×100 pixels). --.

Signed and Sealed this

Thirty-first Day of August, 2004

JON W. DUDAS
*Director of the United States Patent and Trademark Office*